(12) United States Patent
Fockens

(10) Patent No.: US 8,500,815 B2
(45) Date of Patent: Aug. 6, 2013

(54) SHOULDER PROSTHESIS WITH INSERT FOR LOCKING SCREWS

(76) Inventor: Wilko Fockens, Lyons (FR)

( * ) Notice: Subject to any disclaimer, the term of this patent is extended or adjusted under 35 U.S.C. 154(b) by 0 days.

(21) Appl. No.: 13/496,155

(22) PCT Filed: Oct. 1, 2010

(86) PCT No.: PCT/IB2010/002785
§ 371 (c)(1),
(2), (4) Date: Mar. 14, 2012

(87) PCT Pub. No.: WO2011/048486
PCT Pub. Date: Apr. 28, 2011

(65) Prior Publication Data
US 2012/0172992 A1    Jul. 5, 2012

(30) Foreign Application Priority Data

Oct. 23, 2009  (FR) .................................... 09 05097
Dec. 7, 2009  (FR) .................................... 09 05900

(51) Int. Cl.
*A61F 2/40*  (2006.01)
(52) U.S. Cl.
USPC .................................... 623/19.11; 623/19.12
(58) Field of Classification Search
CPC ......................................................... A61F 2/40
USPC ............. 623/19.11–19.14, 22.11, 22.4–22.46
See application file for complete search history.

(56) References Cited

FOREIGN PATENT DOCUMENTS

| EP | 0 940 126 A1 | 9/1999 |
| FR | 2 689 756 A1 | 10/1993 |
| WO | WO 97/39693 A1 | 10/1997 |
| WO | WO 2004/024029 A2 | 3/2004 |

OTHER PUBLICATIONS

International Search Report, Mar. 22, 2011, from International Phase of the instant application.

*Primary Examiner* — Jason-Dennis Stewart
(74) *Attorney, Agent, or Firm* — Jackson Patent Law Office

(57) ABSTRACT

An insert (1) designed for insertion into a central cavity (10) within the upper part of the prosthetic stem (13) of a shoulder prosthesis. The insert (1) is provided with at least one transverse hole (6) that is threaded or provided with an inner retaining rib or any other screw-locking means. The insert (1) is designed for locking of transverse tuberosity bone screws (4) in the same way as a cross-dowel-nut. The outer surface of the prosthetic stem (13) is provided with at least one transverse unthreaded hole (7) communicating with the central cavity (10) in order to allow a sliding passage for the bone screw (4).The insert for a prosthetic humeral head implant of an anatomical shoulder prosthesis is interchangeable with an insert for the cup-shaped humeral implant (18) of a reverse shoulder prosthesis. The insert (1) is provided with a fixation site (8) for a targeting arm.

14 Claims, 6 Drawing Sheets

SHOULDER PROSTHESIS WITH INSERT FOR LOCKING SCREWS

TECHNICAL FIELD

The present invention relates to the field of orthopedic surgery and, more specifically, to the field of joint replacement with shoulder prosthesis in the treatment of complex upper humerus fractures.

BACKGROUND ART

In the present state of art, two totally different types of shoulder prosthesis are routinely implanted, namely the "anatomical" shoulder prosthesis characterized by the presence of a convex-shaped humeral head implant (cooperating with the glenoid cavity of the scapula) and the "reverse" (or "inverted") shoulder prosthesis, characterized by the presence of a concave cup-shaped humeral implant (cooperating with a "glenosphere", which is a hemispherical implant attached onto the glenoid cavity).

Treatment of complex upper humerus fractures in elderly people with osteoporosis is a frequent indication for prosthetic shoulder joint replacement. However, functional results after implantation of "anatomical" shoulder prosthesis on fracture are quite mediocre and inconstant because of a high rate of malunions (bone healing in a non-anatomical position) and nonunions (absence of bone healing) of the tuberosity bone fragments (greater tubercle and lesser tubercle) around the upper part of the prosthetic stem. These tuberosity bone fragments are not only osteoporotic and fragile but also sustain important strains because of movements in the adjacent shoulder joint and because of traction forces from the muscle insertions (rotator cuff) on these tuberosity bone fragments. Therefore, stable fixation of the tuberosity bone fragments onto the prosthetic stem is of utmost importance for optimal bone healing and functional recovery.

Tuberosity bone fragment fixation can be done by means of bone sutures going through smooth holes in the upper part of the prosthetic stem and/or by means of locking bone screws into threaded boreholes. Tuberosity bone fixation by means of bone sutures not only is a meticulous and tedious technique but is also relatively fragile with a high risk for the sutures to cut through the edges of the osteoporotic bone fragments, thus resulting in suture loosening and secondary displacement of the bone fragments. Bone fragment fixation with locking bone screws is more straightforward and is also mechanically stronger, especially if associated with tension band sutures going around the protruding heads of the bone screws.

In case of a bad functional outcome of an anatomical prosthesis on upper humerus fracture, secondary conversion of the anatomical prosthesis into a reverse shoulder prosthesis can be an option. In that case, the prosthetic humeral head implant has to be replaced by the concave cup-shaped humeral implant. Secondary conversion of the prosthesis with conservation of the already implanted intraosseous prosthetic stem is an important advantage, not only for the surgeon, but especially for the patient, because extraction of the already implanted (cemented or osteointegrated) prosthetic stem out of an osteoporotic bone is not only difficult and takes time for the surgeon but also can cause new complicated bone fractures with supplementary morbidity and impairment for the already fragile patient.

Furthermore, because of the mediocre functional results of anatomical shoulder prosthesis on fracture, many surgeons nowadays readily opt for primary implantation of a reverse shoulder prosthesis on fracture. Even in that case, stable tuberosity fixation onto the reverse shoulder prosthesis is still useful in order to obtain optimal recovery of active external rotation.

Therefore it is mandatory that a shoulder prosthesis, specifically designed for fracture treatment, has a "universal" stem, in order to allow implantation of a prosthetic humeral head (anatomical shoulder prosthesis) as well as a humeral cup (reverse shoulder prosthesis). In the present state of art, most existing universal shoulder prosthesis systems are equipped with an inverted Morse taper connection at the upper end of the stem, which means that the conical (male) Morse taper is protruding from the underside of the humeral head implant or from the underside of the humeral cup-shaped implant. Thus, the downwards orientated (male) Morse taper is impacted into the corresponding (female) tapering cavity situated on the upper surface of the prosthetic stem.

The inverted Morse taper connection is to be clearly distinguished from the standard Morse taper connection used in standard anatomical shoulder prosthesis systems. In the standard Morse taper connection, the (male) Morse taper is protruding upwards from the upper surface of the prosthetic stem and is impacted into a (female) tapering cavity on the underside of the humeral head implant. The presence of a standard (upwards orientated) Morse taper connection is totally incompatible with the concave humeral cup-shaped implant of the reverse shoulder prosthesis because of spatial obstruction.

Anchoring bone screw fixation into a threaded borehole across the prosthetic stem is not possible in the presence of an inverted (downwards orientated) Morse taper connection because of the spatial obstruction caused by the male Morse taper inside the upper part of the stem. Indeed, a Morse taper connection can be reinforced with an axial screw, which will reinforce the impaction of the tapering connection, but the Morse taper connection is totally incompatible with a transverse locking screw which would cause loosening of the impacted tapering connection.

In short: in the present state of art, locking screw fixation into threaded boreholes on the prosthetic stem, as described in patents U.S. Pat. No. 6,398,812 and WO2005089678 is only possible on an anatomical shoulder prosthesis with a standard (upwards orientated) Morse taper connection, but this type of prosthesis doesn't allow the surgeon to do primary or secondary conversion into a reverse prosthesis. Therefore, in the present state of art, many surgeons prefer to use universal shoulder prosthesis systems with an inverted (downwards orientated) Morse taper connection, thus losing the ability to use locking bone screws for tuberosity fixation.

In the technique of osteosynthesis with a medullary nail, it appears clearly that the bone screw holding the greater tubercle is best located at the level situated just above to the center of the (imaginary) circle surrounding the humeral head (see FIG. 2). The position of a horizontally orientated bone screw, situated above the center of the humeral head is referred to as the "supra-equatorial" position. In addition, the supra-equatorial bone screw should have a posterior-to-anterior radial orientation of about 30 to 45 degrees to the frontal plane, thus imposing the presence of two different holes for the same screw, depending on the side of implantation (right shoulder or left shoulder). In most of the actual types of prosthetic stems, especially in the "low bulk" stems for fracture treatment, the upper end of the prosthetic stem is very narrow with insufficient space for a (double) supra-equatorial locking borehole.

Fixation of a targeting arm onto the upper part of a prosthetic stem also creates a problem of spatial obstruction. Indeed, fixation of the targeting arm onto the lateral side of the prosthetic stem as described in patents WO2005089678 and EP2002794 precludes reduction of the tuberosity bone fragments around the prosthetic stem. Fixation of the targeting arm onto the upper surface of the prosthetic stem (passing through a hole in the prosthetic head) allows unhindered tuberosity fracture reduction but, in that case, the axial fixation screw of the targeting arm will create obstruction for a horizontally orientated supra-equatorial bone screw.

In the technique of osteosynthesis of fractures of the upper humerus with a medullary nail, the nail is inserted through the lateral part of the native humeral head, the upper end of the nail being located only a few millimeters underneath the cartilage surface. Therefore the junction between the nail and the targeting arm is located at the level of the humeral head, thus leaving sufficient space for a supra-equatorial bone screw anchoring within the upper part of the medullary nail, just beyond the axial fixation screw of the targeting arm. The technical solution which would consist in an elevated knob protruding from the upper surface of the prosthetic stem, in order to allow fixation of the targeting arm together with supra-equatorial screw fixation, would have the inconvenience that this knob would preclude secondary conversion of the anatomical prosthesis into a reverse prosthesis.

The technical solution proposed in patent WO2004024029, consisting of the fixation of a prosthetic humeral head directly onto a medullary nail, has the inconvenience that the presence of the claimed "lateral connection means" considerably reduces the available space for transverse locking bone screws. Furthermore, the lack of osteointegration of the medullary nail with persistent (micro)-movements between the nail and the surrounding bone will result in pain and functional impairment for the patient. This technical solution neither foresees the possibility of secondary conversion into a reverse shoulder prosthesis.

The technical solution proposed in patent FR2909858, consisting in driving bone screws directly into a polyethylene "connecting wedge" disposed around the upper part of a prosthetic stem has the inconvenience of reducing the metallic surface of the prosthetic stem and therefore will decrease the chances for osteointegration together with the additional risk that the micro particles of polyethylene, which are released during the drilling of the holes, might even induce osteolysis.

Patent WO9739693 claims a tri-partite prosthetic stem comprising a lateral part meant for bone screw fixation, in combination with an inverted Morse taper connection for the prosthetic head, seemingly neglecting the abovementioned problems of spatial obstruction.

Therefore, the technical problem to be solved is to allow locking of a bone screw in a supra-equatorial position onto a universal prosthetic stem without reducing the outer osteointegration surface of the stem.

DISCLOSURE OF THE INVENTION

The present invention is an insert, referred to as "anchorage insert", and designed for insertion into a central or axial cavity within the upper part of the prosthetic stem (see FIGS. 1 and 2). The anchorage insert is provided with at least one transverse borehole for the anchorage (or locking) of at least one bone screw, the borehole being threaded or being provided with a retaining rib or any other locking mechanism for bone screws. The anchorage insert for a prosthetic humeral head is interchangeable with an anchorage insert for the cup-shaped humeral implant.

The outer surface of the prosthetic stem is provided with at least one transverse unthreaded borehole communicating with the central cavity in order to allow a sliding passage for the bone screw. After the insertion of the anchorage insert into the central cavity, the unthreaded slide-hole of the prosthetic stem and the locking hole of the anchorage insert are coaxial. Thus, the bone screw passes through the slide-hole of the prosthetic stem into the locking hole of the anchorage insert. Therefore, the anchorage insert within the prosthetic stem is comparable to a cross-dowel-nut fixation system (see FIGS. 3 and 4).

The unthreaded slide-hole of the prosthetic stem also has the practical advantage to facilitate exact alignment of the bone screw with the threaded hole of the anchorage insert. Thus, the slide-hole of the prosthetic stem acts as a second (internal) targeting device completing the function of the targeting arm.

In the preferred embodiment, the upper end of the anchorage insert is provided with a targeting arm fixation site. Therefore, the junction between the anchorage insert and the targeting arm is located at the level of the prosthetic head, significantly higher (more proximally) than the upper surface of the prosthetic stem, thus leaving sufficient space for a supra-equatorial screw fixation. In order to allow fixation of the targeting arm to the upper end of the anchorage insert, the lateral part of the prosthetic humeral head is provided with a large hole or notch.

In another possible (not illustrated) embodiment, the targeting arm is attached directly to the prosthetic humeral head or to the humeral cup-shaped implant.

In the preferred embodiment, the anchorage insert is provided with three locking holes for optimal tuberosity fixation. As mentioned above, the supra-equatorial locking hole ideally has a different radial orientation depending on implantation in a right or left shoulder. Therefore, in the preferred embodiment, the anchorage insert is specific for implantation in a right or a left shoulder. On the contrary, the prosthetic stem is "ambidextrous" and therefore, the number of slide-holes on the prosthetic stem is superior to the number of locking holes on the anchorage implant. The slide-holes are unthreaded and are provided with an osteointegration favoring surface. Thus, the presence of numerous slide-holes on the outer surface of the prosthetic stem increases the available surface for osteointegration, unlike threaded holes that would decrease the osteointegration surface of the stem. In order to promote osteointegration, the unoccupied slide-holes can be filled up with bone graft.

In the preferred embodiment, the anchorage insert is metallic, the transverse borehole being threaded or being provided with a screw locking mechanism. In another possible embodiment the anchorage insert is made out of plastic material, for example polyethylene. In that case it is possible to drill holes into the plastic insert during the surgical procedure, just before implantation. Indeed, the holes should be carefully washed out before implantation in order to avoid dispersion of polyethylene micro-particles into the bone tissue. The holes will become threaded automatically by the use of self-tapping bone screws.

In the preferred embodiment, the anchorage insert is secured within the prosthetic stem by means of a locking security screw. The security screw is driven through a transverse or obliquely orientated threaded borehole and tightened against the anchorage insert, thus avoiding vertical or rotational displacement of the anchorage insert during manipulation of the attached targeting arm until insertion of the bone screws. The security screw also allows using the targeting arm as a handle for the prosthetic stem during implantation. The security screw is optional because the anchorage insert will be automatically locked inside the prosthetic stem by the locking bone screws.

In a possible embodiment of the present invention, the upper part of the anchorage insert is provided with a transverse unthreaded borehole for a transverse near-horizontal coupling-screw for complementary fixation of the prosthetic humeral head. In that case, the prosthetic head is first connected to the prosthetic stem by means of a medially situated (removable) knob (see FIG. 5). In another possible embodiment, the medial side of the anchorage insert is provided with an integrated inclined Morse taper designed for fixation of the prosthetic head (see FIG. 6). The obliquely protruding Morse taper should be in a medial position (to the center of the prosthetic head) in order to avoid spatial obstruction with the supra-equatorial bone screw which has a posterior-to-anterior radial orientation of about 30 to 45 degrees to the frontal plane. Thus, the tip of the supra-equatorial bone screw passes outside the Morse taper and protrudes into a recess on the underside of the humeral head.

According to another possible (not illustrated) embodiment, the anchorage insert is one-piece with the prosthetic head implant In a particular embodiment for reverse shoulder prosthesis, the upper end of the anchorage insert is provided with an inclined platform with a peripheral raised edge for insertion of a cup-shaped humeral bearing component (see FIG. 7). In the case of a polyethylene bearing component, the metallic fixation site for the targeting arm should be in a lateral position in order to avoid impingement with the metallic glenosphere after wearing down of the polyethylene.

In another possible (not illustrated) embodiment, the anchorage insert is one-piece with the cup-shaped humeral bearing component.

Another possible (not illustrated) embodiment of the present invention is a GRAMMONT-type reverse prosthesis with the cup-shaped polyethylene insert being locked within the central cavity of the prosthetic stem and wherein the stem is provided with unthreaded transverse slide-holes, the standard polyethylene insert being thus directly used as an anchorage insert.

According to a particular embodiment, the prosthetic stem has a vertically orientated transfixing axial cavity communicating with the diaphyseal medullary canal, the anchorage insert protruding out from the lower (distal) end of a shortened prosthetic stem (see FIG. 8). In that case the anchorage insert is comparable to a straight medullary osteosynthesis nail going axially through the entire shoulder prosthesis. In this embodiment, the tuberosity bone screws are locked into the upper part of the medullary nail disposed within the prosthetic stem and, vice versa, the medullary nail is locked within the prosthetic stem by the bone screws.

According to possible embodiments, the anchorage insert has a rounded cross section, a polygonal cross section or a rectangular shaped cross section.

The main application of the present invention is treatment of complex upper humerus fractures. Nevertheless, even in the absence of fracture, locking screws advantageously reinforce primary fixation of a cementless prosthetic stem, especially in elderly patients with osteoporosis. Locking screw fixation of the lesser tubercle after osteotomy (of the lesser tubercle) also is an alternative to tenotomy of the subscapularis tendon during surgical approach.

BRIEF DESCRIPTION OF DRAWINGS

The enclosed drawings depict examples of possible and intentionally simplified embodiments in order to allow easy comprehension of the invention and the attached advantages. Therefore it is obvious that these drawings, together with the attached detailed description, cannot be considered limiting the scope of the claimed invention.

DETAILED DESCRIPTION OF PREFERRED EMBODIMENTS

Figures 1, 2:
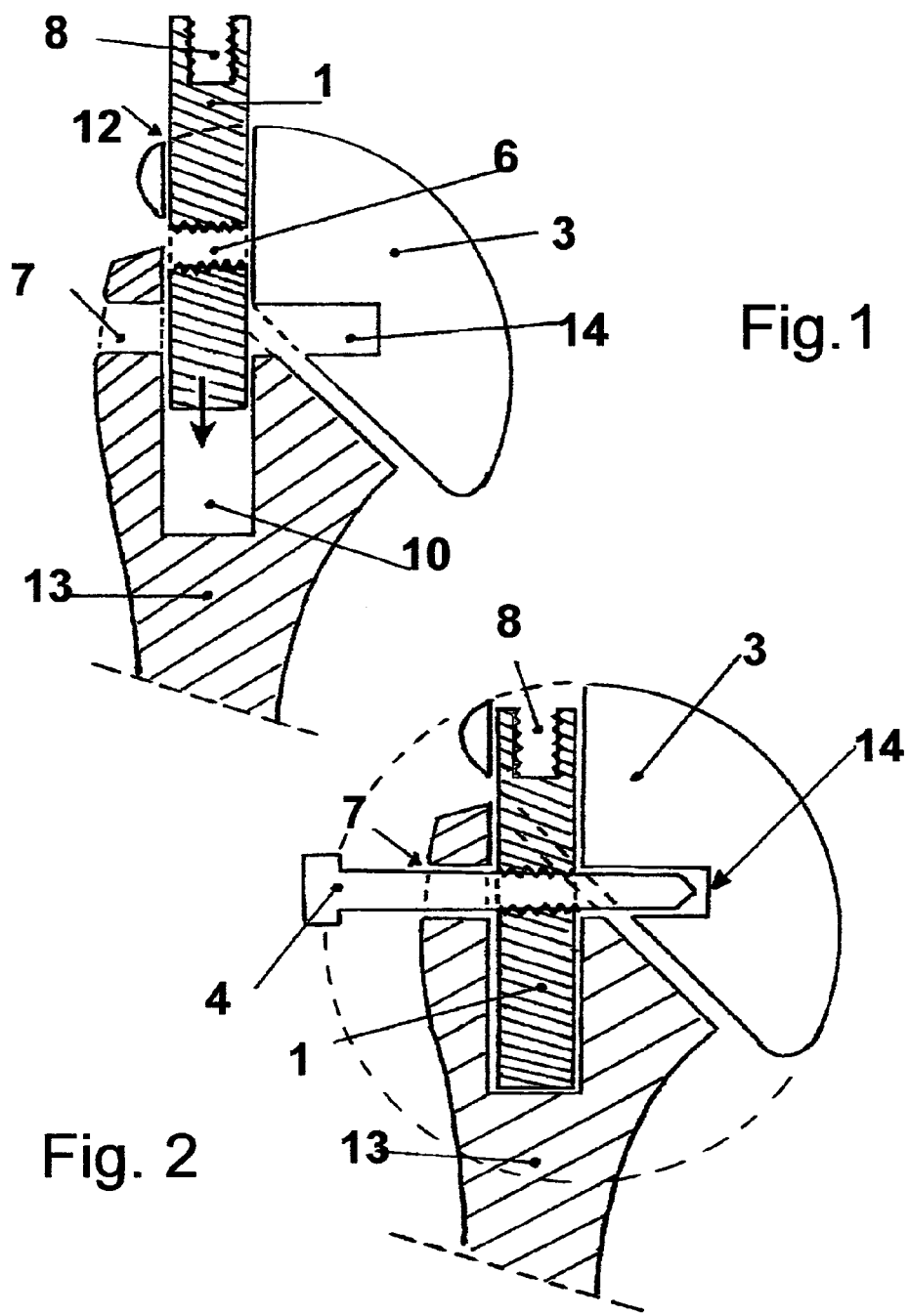
FIGS. 1 and 2 are schematic cross sectional side views of an anatomical shoulder prosthesis illustrating the principle of a locking bone screw fixation onto an anchorage insert disposed within the prosthetic stem.

As illustrated in FIGS. 1 and 2, the anchorage insert (1) is positioned within a central cavity (10) inside the upper part of the prosthetic stem (13). In this embodiment, the central cavity (10) is an axial hole with a vertical orientation. The upper end of the anchorage insert (1) is provided with a fixation site (8) for the targeting arm. The prosthetic humeral head (3) is provided, at its lateral side, with a vertical hole (12) that is coaxial with the central cavity (10) and designed to allow secondary insertion of the anchorage insert (1) after connection of the prosthetic humeral head (3) to the prosthetic stem (13). The upper part of the prosthetic stem (13) is also provided, on its outer surface, with at least one transverse smooth (unthreaded) borehole (7) having a near-horizontal orientation. The smooth transverse borehole (7), referred to as "slide-hole", communicates with the central cavity (10) and is designed for the sliding passage of a bone screw (4). The anchorage insert (1) has at least one transverse borehole (6), referred to as "locking hole", which is threaded or provided with any other screw-locking mechanism such as, for example, a simple retaining rib. After insertion of the anchorage insert (1) into the axial cavity (10) of the prosthetic stem (13), the locking hole (6) of the anchorage insert (1) is in coaxial position with the slide-hole (7) of the prosthetic stem (13), thus allowing introduction and locking (anchoring) of the bone screw (4) within the anchorage insert (1).

FIG. 2 also shows the (imaginary) circle that circumscribes the convex surface of the humeral head, the "equator" being defined as the horizontal plane going through the center of the circumscribing sphere. The position of the bone screw (4) in FIG. 2, situated above the center of the circumscribing sphere, is referred to as the "supra-equatorial" position. At the supra-equatorial level, the upper end of the prosthetic stem (13) is rather narrow and the tip of the supra-equatorial bone screw (4) protrudes into a recess (14) situated on the under surface of the prosthetic head (3)

Figure 3:
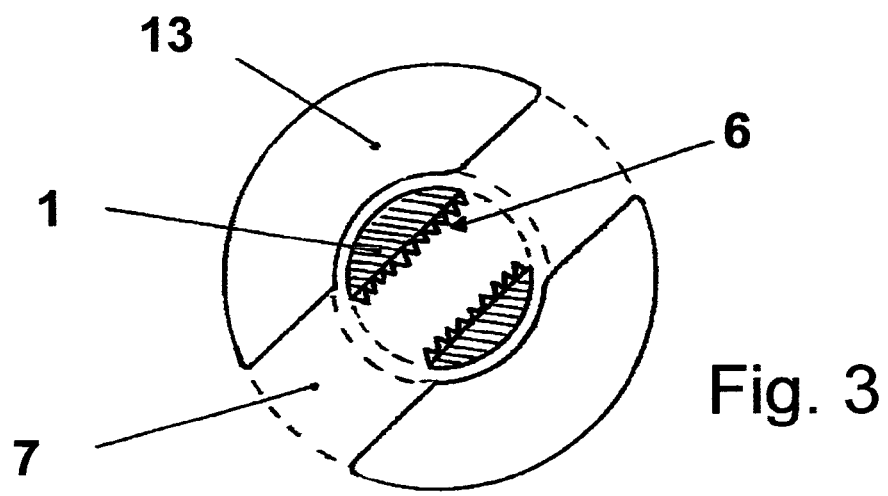
FIGS. 3 and 4 are schematic transverse cross sectional views illustrating the basic principle of a cross-dowel-nut fixation system.
Figure 4:
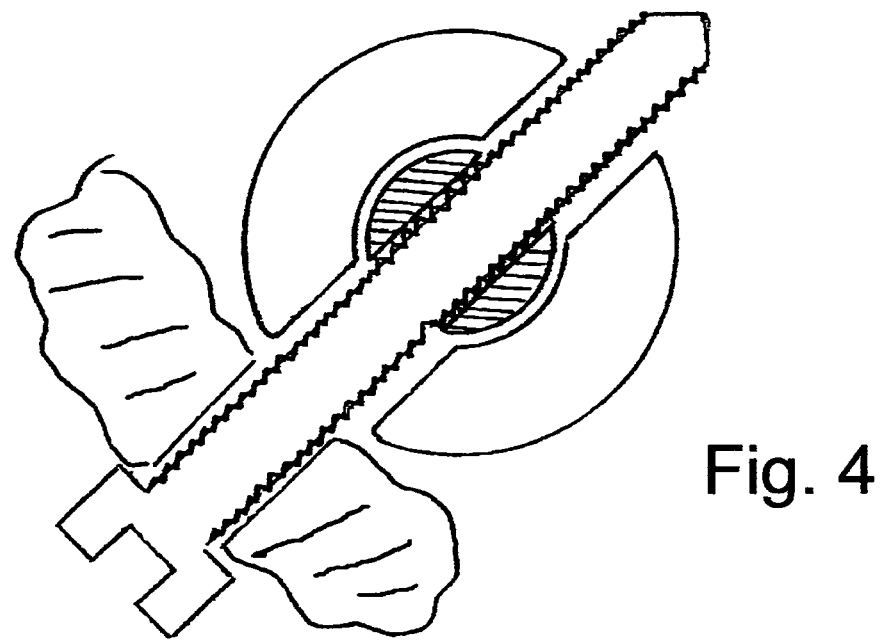

As illustrated in FIGS. 3 and 4, the anchorage insert (1) disposed within the central or axial cavity (10) of the prosthetic stem (13) is similar to a cross-dowel-nut. The thread inside the locking hole (6) retains the screw that is freely sliding within the slide-hole (7) of the prosthetic stem (13).

Figure 5:
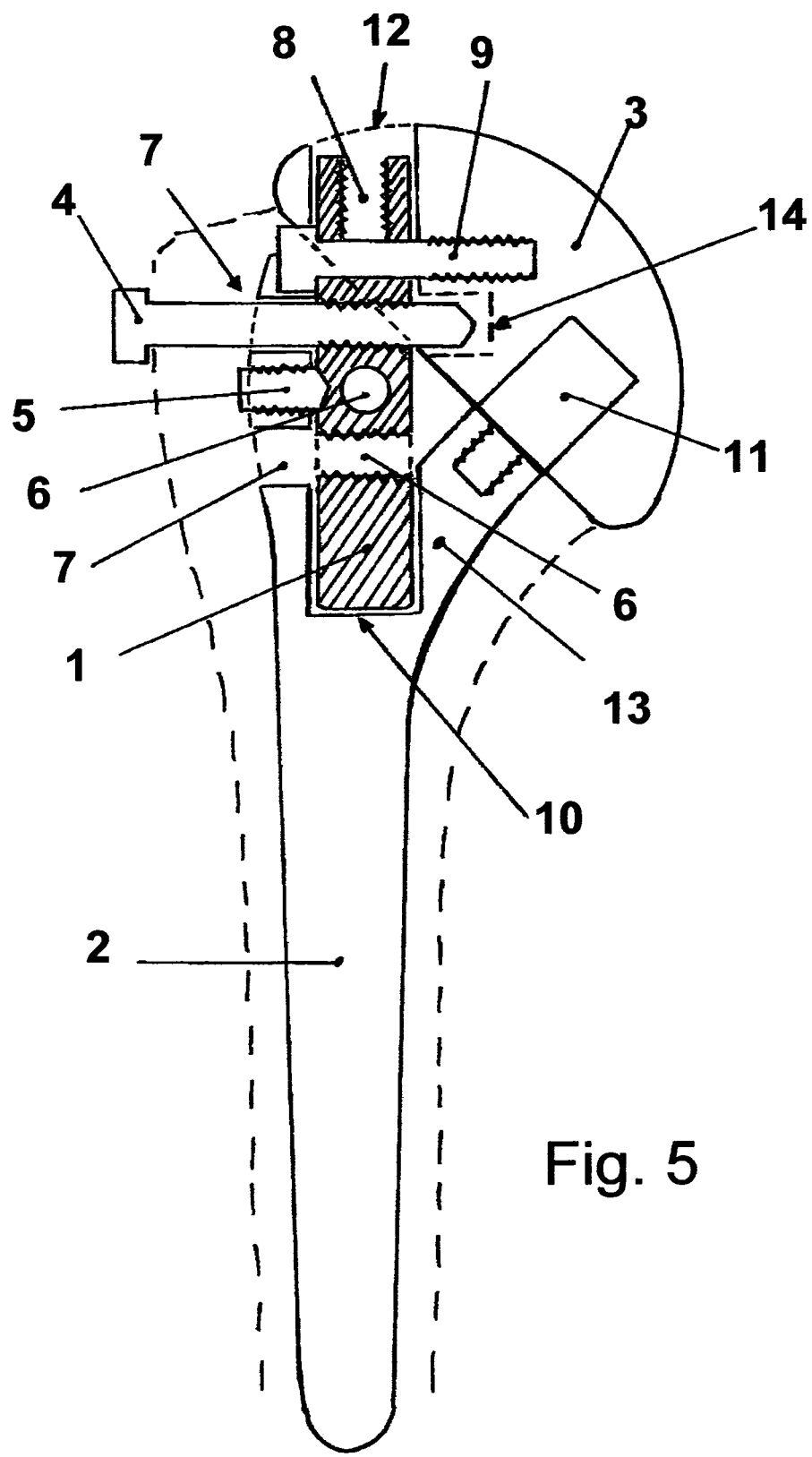
FIG. 5 is a simplified cross sectional side view of an embodiment of an anatomical shoulder prosthesis with a prosthetic humeral head connected to the anchorage insert by means of a transverse coupling screw.

FIG. 5 shows a possible embodiment of an anatomical shoulder prosthesis where the upper part of the anchorage insert (1) is provided with a transverse unthreaded borehole designed for the passage of a horizontally orientated "coupling screw" (9) for the fixation of the prosthetic humeral head (3) to the anchorage insert (1). In the illustrated embodiment (FIG. 5) the prosthetic humeral head (3) is previously connected to the prosthetic stem (13) by means of a slide-fitting around a removable cylindrical knob (11) situated on the medial side of the upper surface of the prosthetic stem (13). The cylindrical knob (11) can also be a Morse taper.

The outer surface of the prosthetic stem (13) is provided with a transverse threaded borehole designed for insertion of a security locking screw (5) which is tightened against the anchorage insert (1), within the central cavity (10). The security screw (5) is designed to avoid vertical and rotational mobility of the anchorage insert (1) inside the central cavity (10) until bone screw insertion. In the illustrated embodiment (FIG. 5) the anchorage insert (1) is provided with three locking holes (6) for three locking bone screws (4) for tuberosity fixation. In reality, the supra-equatorial bone screw (4) isn't situated in the frontal cross sectional plane (as illustrated for simplification) but is orientated in a posterior-to-anterior direction of about 30 to 45 degrees to the frontal plane. The bone screw for the fixation of the lesser tubercle has an anterior-to-posterior orientation of about 60 to 90 degrees to the frontal plane. Because of the presence of locking holes (6) with different, non orthogonal, radial orientations, the anchorage insert (1) isn't symmetrical. Therefore a different anchorage insert (1) has to be used depending on implantation in a right or a left shoulder. The prosthetic stem (13) is voluminous enough to be provided with symmetrically disposed pairs of slide-holes (7) allowing "ambidextrous" implantation. Therefore, the number of slide-holes (7) on the upper part of the prosthetic stem (13) is superior to the number of locking holes (6) on the anchorage insert (1). The slide-holes (7) are unthreaded and therefore provided with an osteointegration favoring surface. Thus, the unoccupied slide-holes (7) participate in increasing the osteointegration surface of the prosthetic stem (13) and can be filled up with bone graft from the native humeral head. In the preferred embodiment (not illustrated), the lower (distal) end of the prosthetic stem (2) is provided with smooth transverse bore-holes designed for distal locking of the prosthetic stem (13), at the end of the surgical procedure, by means of bone screws inserted through the targeting arm, in a similar way as distal locking of a medullary nail. In the preferred embodiment, the anchorage insert (1) is metallic with threaded locking holes (6) or with holes provided with a simple retaining rib, but in the illustrated embodiment, the anchorage insert (1) can also be made out of plastic material such as polyethylene. In that case, the surgeon will drill holes in the plastic insert just before implantation. By using self-tapping bone screws, the screws will automatically create a retaining thread in the plastic material.

Figure 6:
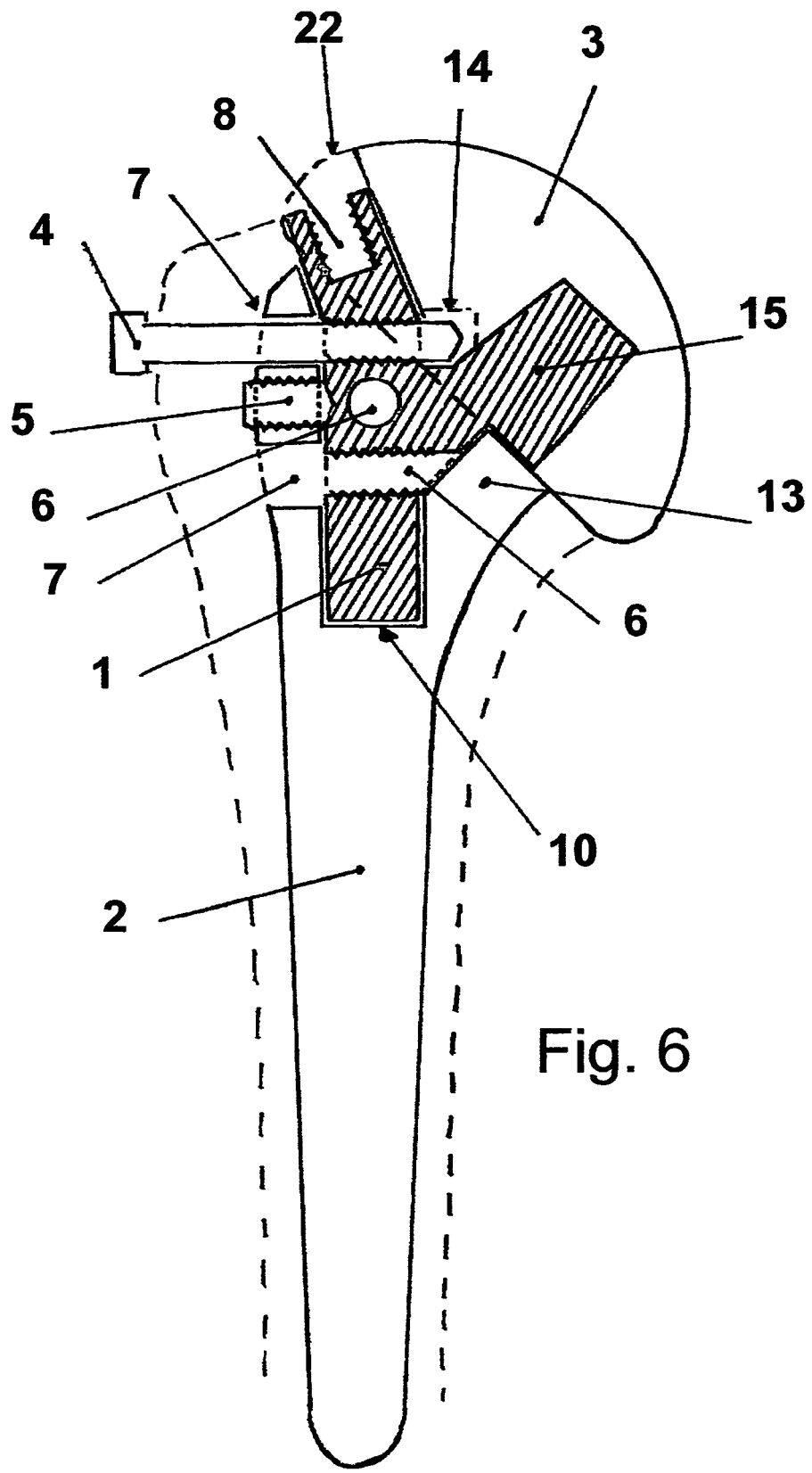
FIG. 6 is a cross sectional side view of an embodiment of an anatomical shoulder prosthesis with an anchorage insert provided with a Morse taper for connection to the prosthetic humeral head.

In the embodiment illustrated in FIG. 6, the medial side of the anchorage insert (1) is provided with an integrated inclined Morse taper (15) designed to fix the prosthetic head (3). The obliquely protruding Morse taper (15) should be in a medial position in order to avoid spatial obstruction with the supra-equatorial bone screw (4) which has a posterior-to-anterior radial orientation of about 30 to 45 degrees to the frontal plane. Thus, the tip of the supra-equatorial bone screw (4) passes outside the Morse taper (15) into a recess (14) on the underside of the humeral head (3). For this embodiment, the assembly of the prosthetic head (3) onto the anchorage insert (1), through impaction of the Morse taper, is done before implantation. The lateral edge of the prosthetic humeral head (3) has a large notch (22) for the targeting arm and the corresponding fixation site (8).

Figure 7:
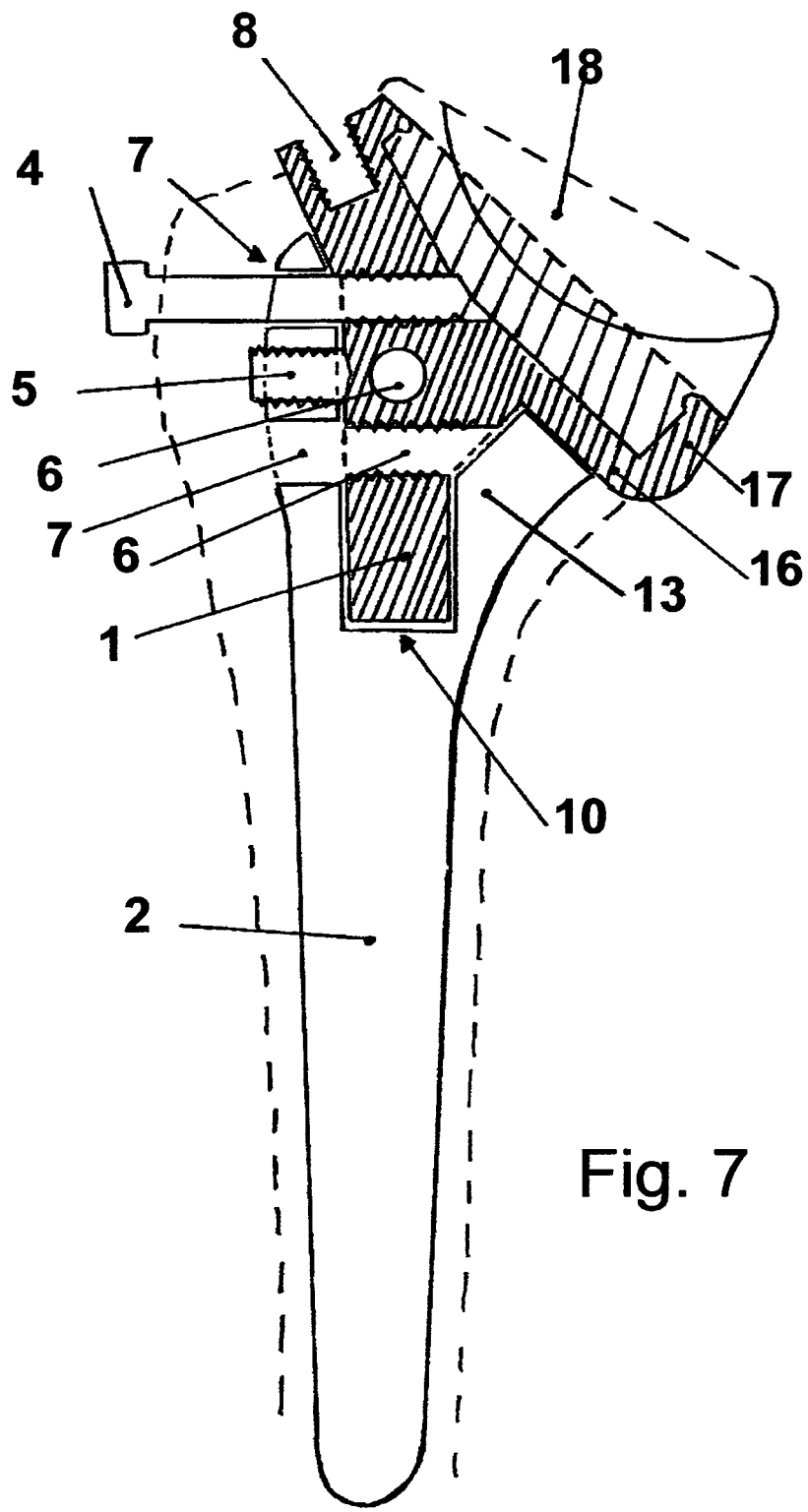
FIG. 7 is a cross sectional side view of an embodiment of a reverse shoulder prosthesis, illustrating the anchorage insert with a platform for fixation of a cup-shaped humeral implant.

FIG. 7 illustrates the preferred embodiment for a reverse shoulder prosthesis wherein the upper end of the anchorage insert (1) is provided with a rounded inclined platform (16) with a peripheral raised edge (17) designed for insertion of a (polyethylene) cup-shaped humeral bearing component (18). The targeting arm fixation site (8) is in a lateral position in order to avoid impingement with the metallic glenosphere after wearing down of the polyethylene.

Figure 8:
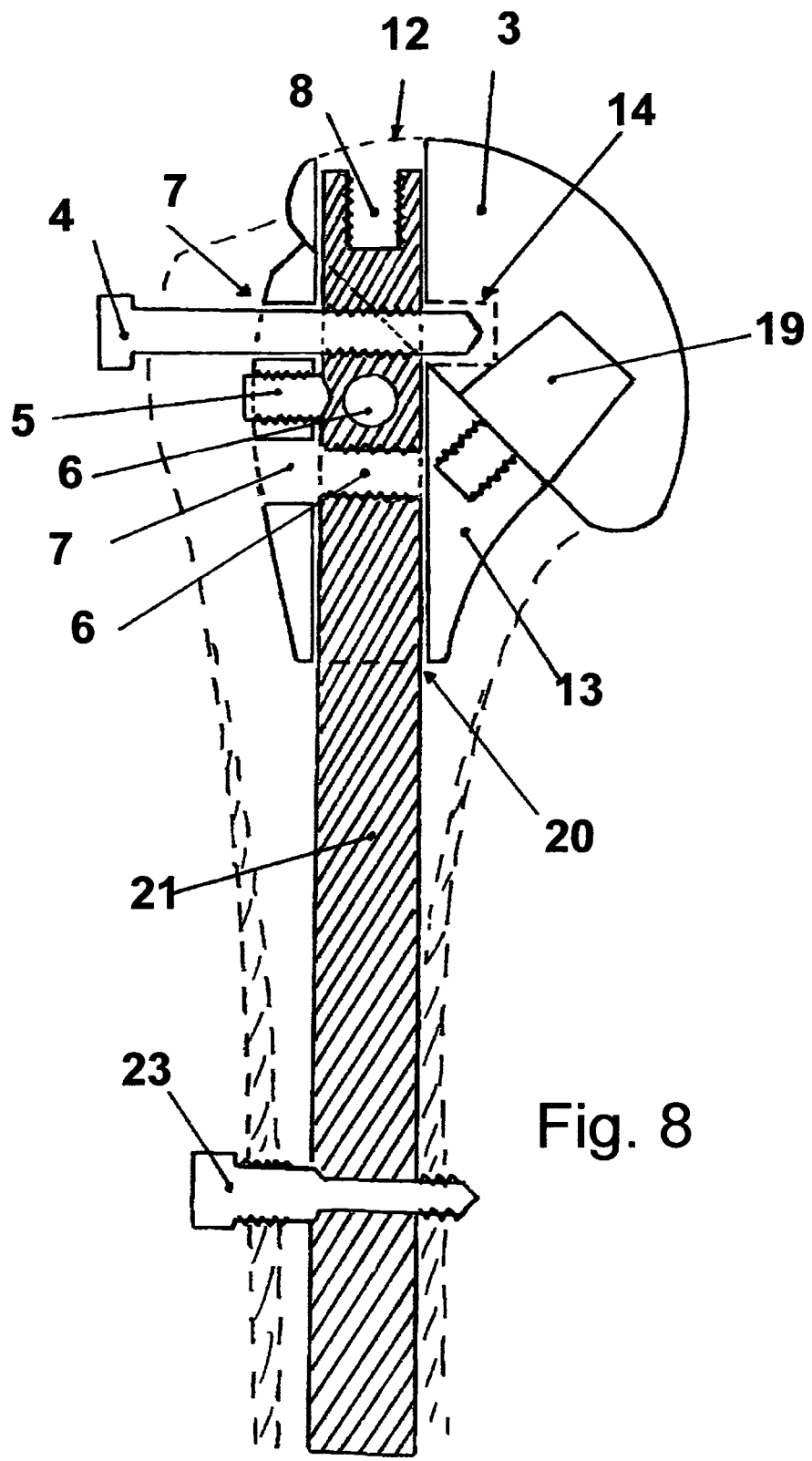
FIG. 8 is a cross sectional side view of an embodiment of an anatomical shoulder prosthesis with the anchorage insert being a medullary nail for osteosynthesis.

FIG. 8 illustrates a particular embodiment combining a shortened prosthetic stem (13) provided with a transfixing axial hole (20), the anchorage insert being a straight medullary nail (21) going entirely through the prosthetic stem (13) into the medullary canal. In this embodiment, the bone screws (4) are locked within the locking holes (6) situated on the upper part of the medullary nail (21). Vice versa, the medullary nail (21) is locked within the prosthetic stem (13) by means of the transverse locking bone screws (4). In this illustration the prosthetic humeral head (3) is connected to the prosthetic stem (13) by means of a (removable) Morse taper (19), but alternative connection means are possible, for example fitting on a cylindrical knob combined with a transverse coupling-screw (see FIG. 5) or a slide-fitting (not illustrated). The medullary nail necessarily has a small diameter (7 to 9 millimeters). Ideally, the distal locking of the medullary nail (21) is done by means of key-screws (23), thus locking the nail against the medial bone cortex.

INDUSTRIAL APPLICABILITY

The claimed shoulder prosthesis is meant for shoulder joint replacement in the surgical treatment of complex upper humerus fractures and in the surgical treatment of osteoarthritis.

The invention claimed is:
1. Shoulder prosthesis, —comprising: (i) a prosthetic stem with an upper surface provided with a central or axial cavity having a near-vertical orientation, said central cavity communicating with a transverse smooth unthreaded hole having a near-horizontal radial orientation, said smooth hole being designed for the passage of a transverse tuberosity bone fixation screw, (ii) a humeral articular bearing component designed for cooperation with the glenoid cavity or with a glenoid implant, said humeral articular bearing component being either a convex articular implant of an "anatomical shoulder prosthesis" or a concave articular implant of a "reverse shoulder prosthesis", (iii) an insert, referred to as "anchorage insert", designed for insertion into the central cavity of the prosthetic stem, —wherein said anchorage insert has a transverse hole, referred to as "locking hole", provided with a screw-locking means, said anchorage insert being designed for locking of the tuberosity bone fixation screw.

2. Shoulder prosthesis according to claim 1, wherein said anchorage insert is metallic and provided with a locking hole equipped with a thread, a retaining rib or any other screw locking means.

3. Shoulder prosthesis according to claim 1, wherein said anchorage insert is made out of plastic material, for example polyethylene.

4. Shoulder prosthesis according to claim 1, wherein the upper end of the said anchorage insert is provided with a fixation site for a targeting arm.

5. Shoulder prosthesis according to claim 1, wherein said anchorage insert has a rounded, polygonal or rectangular cross section.

6. Shoulder prosthesis according to claim 1, wherein said anchorage insert is locked within the central cavity of the prosthetic stem by means of a transversely or obliquely orientated security screw.

7. Shoulder prosthesis according to claim 1, wherein the upper part of said anchorage insert is provided with a smooth transverse hole for the passage of a coupling screw with a near-horizontal orientation, designed to connect the convex articular implant to the anchorage insert.

8. Shoulder prosthesis according to claim 1, wherein said anchorage insert is metallic and provided, on its medial side, with a Morse taper for connection to the convex articular implant.

9. Shoulder prosthesis according to claim 1, wherein said anchorage insert is one-piece with the convex articular implant.

10. Shoulder prosthesis according to claim 1, wherein said anchorage insert is metallic and provided, at its upper end, with a platform with a raised edge designed for fixation of a concave articular implant.

11. Shoulder prosthesis according to claim 1, wherein said anchorage insert is one-piece with the concave articular implant.

12. Shoulder prosthesis according to claim 1, wherein the lateral edge of said convex articular implant is provided with a large hole or a large notch for the targeting arm.

13. Shoulder prosthesis according to claim 1, wherein the underside of said convex articular implant is provided with a recess for the protruding bone screw.

14. Shoulder prosthesis according to claim 1, wherein said anchorage insert is a straight medullary nail for osteosynthesis and wherein the central cavity of the prosthetic stem is a transfixing axial hole, communicating with the medullary canal of the humerus.

\* \* \* \* \*